US009412022B2

(12) United States Patent
Flom et al.

(10) Patent No.: US 9,412,022 B2
(45) Date of Patent: Aug. 9, 2016

(54) IRIS IDENTIFICATION SYSTEM AND METHOD

(71) Applicants: Leonard Flom, Fairfield, CT (US); Ophir Almog, Ramat Gan (IL)

(72) Inventors: Leonard Flom, Fairfield, CT (US); Ophir Almog, Ramat Gan (IL)

(*) Notice: Subject to any disclaimer, the term of this patent is extended or adjusted under 35 U.S.C. 154(b) by 352 days.

(21) Appl. No.: 13/958,180

(22) Filed: Aug. 2, 2013

(65) Prior Publication Data

US 2014/0064575 A1 Mar. 6, 2014

Related U.S. Application Data

(60) Provisional application No. 61/697,598, filed on Sep. 6, 2012.

(51) Int. Cl.
*G06K 9/00* (2006.01)
*G06K 9/46* (2006.01)
*A61B 5/117* (2016.01)

(52) U.S. Cl.
CPC .......... *G06K 9/00617* (2013.01); *G06K 9/0061* (2013.01); *G06K 9/00885* (2013.01); *G06K 9/00892* (2013.01); *G06K 9/4609* (2013.01); *A61B 5/1176* (2013.01); *G06K 9/00281* (2013.01); *G06K 9/00597* (2013.01)

(58) Field of Classification Search
CPC .......... G06K 9/00885; G06K 9/00892; G06K 9/00221; G06K 9/00281; G06K 9/00597; G06K 9/00617; G06T 2207/30196; A61B 5/1176; G06F 21/32
USPC .................. 382/115, 116, 117, 118
See application file for complete search history.

(56) References Cited

U.S. PATENT DOCUMENTS

| 4,641,349 | A | 2/1987 | Flom et al. |
| 5,291,560 | A | 3/1994 | Daugman |
| 2004/0114781 | A1 | 6/2004 | Cho |
| 2007/0078908 | A1 | 4/2007 | Rohatgi et al. |
| 2008/0285813 | A1 | 11/2008 | Holm |
| 2009/0220126 | A1* | 9/2009 | Claret-Tournier et al. ... 382/117 |
| 2010/0189313 | A1* | 7/2010 | Prokoski ....................... 382/118 |
| 2011/0188778 | A1 | 8/2011 | Wiesenfarth |
| 2011/0280451 | A1 | 11/2011 | Sarkar |
| 2012/0082352 | A1 | 4/2012 | Hundley et al. |
| 2013/0236066 | A1* | 9/2013 | Shubinsky et al. ............ 382/115 |

FOREIGN PATENT DOCUMENTS

| WO | WO0116710 A1 * | 10/2001 |
| WO | 2011016710 A1 | 2/2011 |

OTHER PUBLICATIONS

Sudha, et al. IEEE Multi-conference on Systems and controls: Oct. 2007.*

(Continued)

*Primary Examiner* — Michael A Newman
(74) *Attorney, Agent, or Firm* — St. Onge Steward Johnston & Reens, LLC

(57) ABSTRACT

A method for biometric recognition may be employed on multiple biometrics, including irises and ears. The method includes decomposing the radiometric profile of each line of an image into a plurality of wavelets using a wavelet transform process. A unique signal is calculated using the plurality of wavelets. A template is assembled using the signal and areas of interest in the template are identified. The template is then compared to a second template using the plurality of areas of interest.

48 Claims, 10 Drawing Sheets

(56) References Cited

OTHER PUBLICATIONS

Mishra, et al. "Human Recognition Using Fusion of IRIS and Ear Data." International Conference on Methods and Models in Computer Science (2009): 1-5.*

Burget et al. "Chapter 13, Ear Biometrics in Biometrics: Personal Identification in Networked Society," Kluwer Academic Publishers, Boston (1999): 273-285.*

International Search Report & Written Opinion of the International Searching Authority Application No. PCT/US2013/056728 Completed: Feb. 20, 2014; Mailing Date: Mar. 6, 2014 9 pages.

* cited by examiner

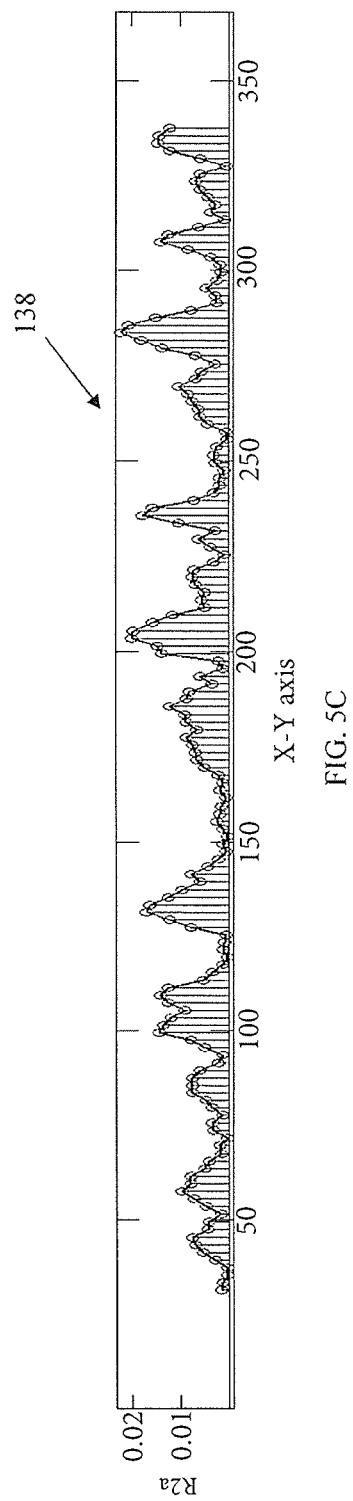

IRIS IDENTIFICATION SYSTEM AND METHOD

FIELD OF THE INVENTION

The present teachings relate generally to biometric identification.

BACKGROUND OF THE INVENTION

Iris recognition is a form of biometric identification (ID) that uses mathematical pattern-recognition techniques on an image of an iris. The iris is a preferable body part to use for biometric ID because it contains complex patterns that are unique and can be seen from a distance. Traditional camera technology may be used to capture an image of an iris, often with subtle infrared illumination.

In order to isolate the iris, an algorithm first localizes the inner and outer boundaries of the iris (e.g., pupil and limbus). Eyelids, eyelashes, and specular reflections that often occlude parts of the iris may then be detected and excluded. Once the iris is isolated, statistical algorithms may be used to create a digital code from patterns found in the iris. These codes may be compared with stored codes in order to identify an individual.

U.S. Pat. No. 4,641,349, entitled "Iris Recognition Technology," the content of which is incorporate by reference in its entirety, discloses a system and method for iris recognition. In particular, it discloses illuminating an iris to a particular size and extracting descriptors which can then be compared against those of a stored iris. This was a pioneering patent in the field of iris recognition developed by Dr. Flom, a named inventor on the current application.

U.S. Pat. No. 5,291,560, entitled "Biometric personal identification system based on iris analysis," the content of which is incorporate by reference in its entirety, discloses another algorithm for iris recognition. In particular, it discloses extracting a bit pattern (an iris code) that encodes information from an iris image. A Gabor wavelet transform is used to filter the image and the result is a set of complex numbers that carry local amplitude and phase information about the iris pattern. For identification (e.g., one-to-many matching) or verification (e.g., one-to-one matching), the iris code can be compared to stored iris codes in a database. If the Hamming distance between the two codes is below a decision threshold, a positive identification has effectively been made.

However, known methods of iris recognition are susceptible to error. For example, a comparison of multiple images of the same iris may result in false negatives (or false positives between different iris images) because the images may be taken using different illumination intensities, with different camera lenses, or at different illumination angles or distances. Differences in ambient conditions make comparison of two images unreliable.

In addition, known methods are not capable of enrolling multiple biometrics. For example, some people may not have irises due to a medical condition (e.g., corneal blindness). In addition, newborn babies do not yet have developed irises and, as a result, known methods for iris recognition cannot be used to identify them.

Therefore, it would be beneficial to have a superior system and method for biometric identification. In particular, it is desirable to have a system for biometric identification capable of being employed on multiple forms of biometrics, for example, irises, ears, and fingerprints.

SUMMARY OF THE INVENTION

The needs set forth herein as well as further and other needs and advantages are addressed by the present embodiments, which illustrate solutions and advantages described below.

The method of the present embodiment includes the steps, but is not limited to, decomposing a profile of an image into a plurality of wavelets using a wavelet transform process, calculating a signal using the profile and the plurality of wavelets, assembling a template using the signal, identifying a plurality of areas of interest in the template, and comparing the template to a second template using the plurality of areas of interest. The image may be an image of a mother's iris and the method repeated on a second image of a child's ear to confirm a relationship between the mother and the child.

The system of the present embodiment includes, but is not limited to, a computer and a database in electronic communication with the computer. Calculator software executing on the computer decomposes at least one profile of at least one image into a plurality of wavelets using a wavelet transform process and calculates at least one signal using the at least one profile and the plurality of wavelets. Coder software executing on the computer assembles at least one template using the at least one signal and identifies a plurality of areas of interest in the at least one template. Identification software executing on the computer compares the at least one template to at least one second template using the plurality of areas of interest, the at least one second template stored in the database. Other embodiments of the system and method are described in detail below and are also part of the present teachings.

For a better understanding of the present embodiments, together with other and further aspects thereof, reference is made to the accompanying drawings and detailed description, and its scope will be pointed out in the appended claims.

BRIEF DESCRIPTION OF THE DRAWINGS

FIG. 5C depicts a signal calculated by dividing the radiometric profile by the wavelet transform levels of FIG. 5B.

DETAILED DESCRIPTION OF THE INVENTION

Figure 1A:
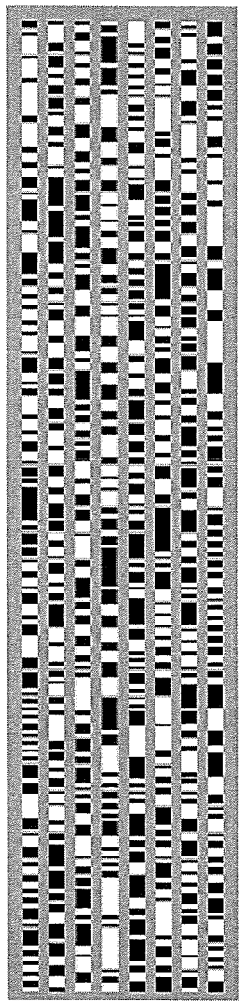
FIG. 1A depicts an example of an iris code created from an iris image using known methods in the art.

The present teachings are described more fully hereinafter with reference to the accompanying drawings, in which the present embodiments are shown. The following description is presented for illustrative purposes only and the present teachings should not be limited to these embodiments.

One benefit of the present teachings is the ability to utilize the algorithm on multiple biometrics. For example, it may be used on irises, ears, and fingerprints, although not limited thereto. Previous methods are not able to do this and to the inventors' knowledge this has not been done before. It is believed that the present teachings are the only non-contact form of biometric identification that permits this combination of identification. Enrollment of multiple biometrics provides statistical advantages, since not only can both of a person's irises be identified, but both of their ears as well. As a result, the risk of false positives can be reduced if a backup biometric is used.

This unique ability of the present teachings is also important to enable the enrollment and recognition of newborn babies. There is not sufficient information from newborn irides due to amorphous newborn irides structure at birth. Iris embryological maturation occurs post-partum for 9 months rather than in uterus. However, there is sufficient differentiation between ears of newborn babies to permit enrollment and recognition and statistical differentiation between other newborns. As a result, one use for the present teachings is to enroll newborn babies and their mothers at birth to help prevent abductions. Newborns can later (e.g., sometime between birth and 9 months, etc.) be enrolled again using the same algorithm on their developing irises to establish identification permanently throughout life.

There are a number of known methods of biometric identification. Iris recognition is preferable because it is non-contact and thus less intrusive over forms that require a subject to come in physical contact with a machine, such as fingerprint identification, or that require an invasive procedure, such as DNA testing.

Other forms of non-contact identification include voice and face recognition. However, the iris may be preferable over these because its structure is generally stable throughout life, whereas a person's face or voice may change. The iris is also stable because it is internal and protected, yet externally visible. This distinguishes it from fingerprints, which can be difficult to recognize after years of certain types of manual labor. Further, the iris is mostly flat, and its geometric configuration is controlled by two complementary muscles (e.g., the sphincter pupillae and dilator pupillae) that control the diameter of the pupil. This makes the iris shape far more predictable than, for instance, that of the face.

Iris recognition also provides a large amount of information and is therefore a more dependable form of identification (e.g., less vulnerable to false positives or negatives). The iris has a fine texture that is determined randomly during embryonic gestation. Like the fingerprint, it is very hard to prove that the iris is unique. However, there are so many factors that go into the formation of these textures that the chance of false matches is extremely low. Even genetically identical individuals have completely independent iris textures.

Performing an iris scan may be similar to taking a photograph and can be performed from various distances, including from about 10 cm to many meters away, depending on the camera technology. There is no need for the person being identified to touch any equipment, thereby eliminating an objection that has been raised in some cultures against fingerprint scanners, where a finger has to touch a surface, or retinal scanning, where the eye must be brought very close to an eyepiece (like looking into a microscope).

Referring now to FIG. 1A, shown is an example of an iris code created from an iris image using known methods in the art. U.S. Pat. No. 5,291,560 discloses a system for iris recognition in which the iris is encoded by dividing it into eight concentric rings of data, which are then formatted into 8 lines of encoded data, as shown in FIG. 1A. The code is then compared to other codes similarly created. The Hamming Distance is used to compare codes. The Hamming Distance is a mathematical algorithm that measures the number of positions at which two sets of information are different.

Figure 1B:
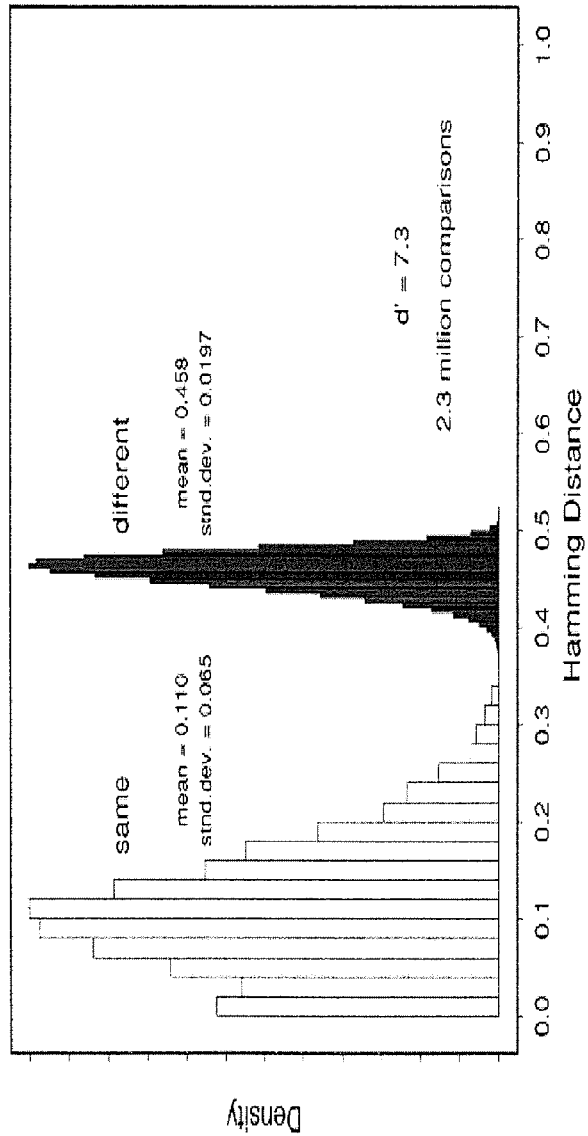
FIG. 1B depicts a graph of Hamming Distance comparisons between the same (left side of graph) and different (right side of graph) irises.

Referring now to FIG. 1B, shown is a graph of Hamming Distance comparisons between the same (left side of graph) and different (right side of graph) irises. FIG. 1B is taken from John Daugman's paper "How Iris Recognition Works," the content of which is incorporate by reference in its entirety. John Daugman is the inventor of U.S. Pat. No. 5,291,560, which uses the Hamming Distance as a recognition rule to count how many pixels are dissimilar between two iris images. If the Hamming Distance between two iris codes is less than 0.3, for example, they may be considered a match. As shown in FIG. 1B, there may be a large variance in Hamming Distance comparisons between even the same irises due to varying environmental conditions.

One problem with previous methods of iris recognition, such as that disclosed in U.S. Pat. No. 5,291,560, is that the intensity and angle of ambient light (e.g., acquisition conditions) affect the collection of information and, as a result, reliability. For example, different intensities of light and distances from the iris may yield differences in images, making comparing image to image difficult. Although "noise" due to varying conditions can be addressed in some respects by modulating an iris image with filters, filters may also reduce the amount of information in the image. Thus, comparing the data from two iris encodings using known methods is difficult and susceptible to error.

Depending upon the acceptable Hamming Distance between two irises (e.g., <0.3) in previous methods, there is a variable potential for false positives or false negatives. There may be a large variance due to the amount of data collected from the iris, coupled with the reliance on a dissimilarity index (Hamming Distance). A dilated pupil may reduce the amount of available information for pupil matching and lead to more false positives. Alcohol consumption and drug use, for example, cause recognition degradation as the pupil dilates/constricts, causing deformation in the iris pattern. Research conducted by one of the inventors, Dr. Flom, indicates that dilation beyond 7.5 mm reduces the effectiveness of prior algorithms such as that disclosed in U.S. Pat. No. 5,291, 560 to Daugman. In addition, dark brown eyes may have poorer information in visible light because a captured image is fairly uniform.

Imposters may employ deception techniques with previous methods of iris recognition, such as dot matrix (e.g., patterned) contact lenses, which throw off the ability to accurately encode an iris. Imposters may also employ scleral lenses comprising artificial eyes with an iris painted on. Many currently available commercial iris scanners can be fooled by a high quality image of an iris in place of the real thing. Criminals could exploit this flaw to steal the identities of others. The accuracy of scanners can also be affected by changes in lighting.

Figure 2:
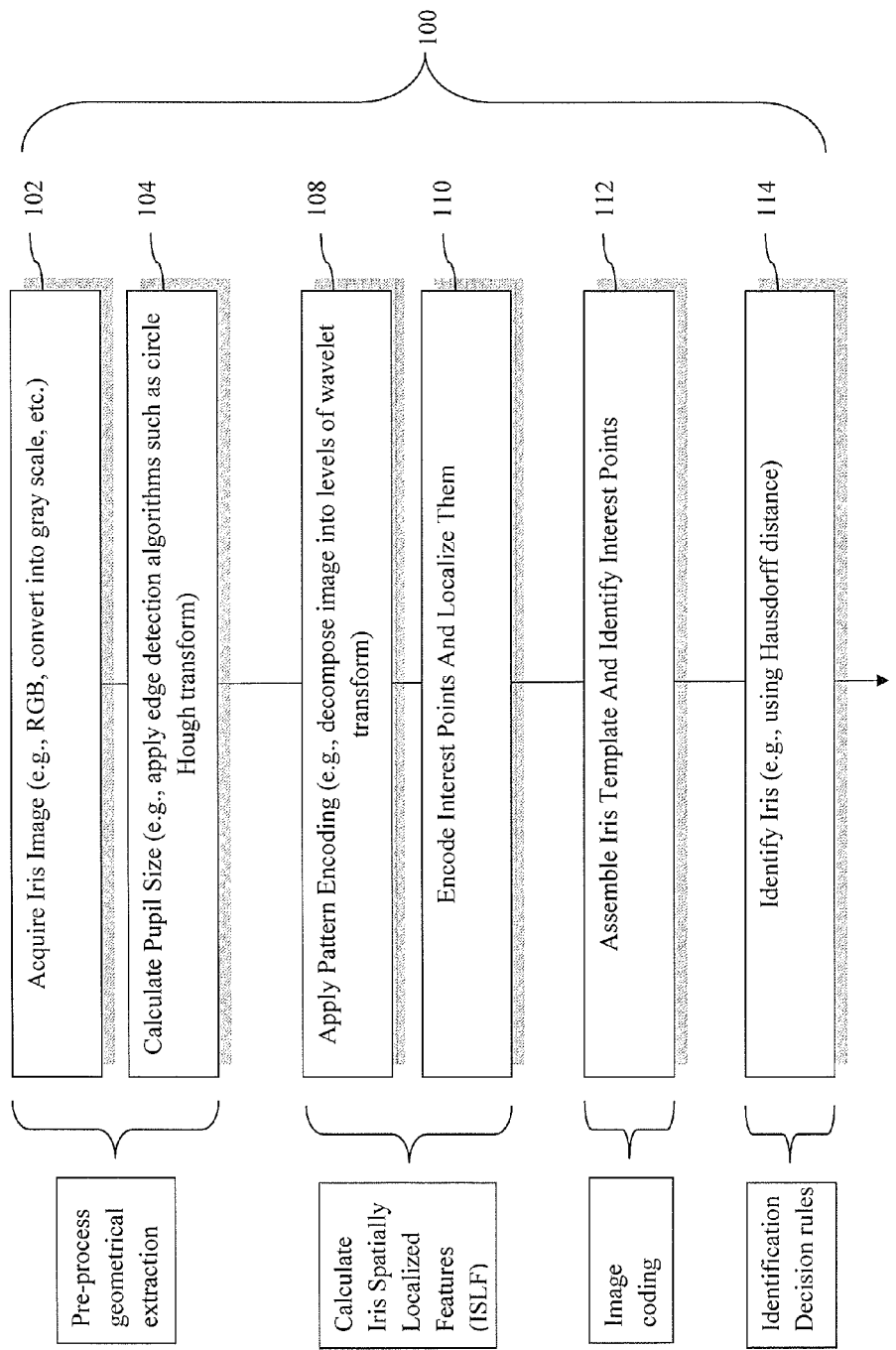
FIG. 2 depicts one embodiment of a method of biometric recognition according to the present teachings.

Referring now to FIG. 2, shown is one embodiment of a method of biometric recognition according to the present teachings. In order to address problems with previous methods of iris recognition, the method may perform spatial analysis, whereby the coded image is spatially localized and, as a result, is less sensitive to illumination conditions and pupil dilations. The resulting iris encoding (e.g., "iris template") can then be normalized for comparison with stored images. An additional benefit of the present teachings is that they may be applied to other biometrics (e.g., ears, etc.). However, the present teachings will be discussed below first with reference to irises.

Since the iris shape is circular, two images for comparison may be taken (or corrected) to have the same orientation coherently to the eye axis (e.g., horizontal and vertical). This means that areas of interest (e.g., descriptors) should be located angular similarly. As a result, the constriction of all interested information (spatial points or shapes) would be proportionally scaled (e.g., invariant to pupil dilations).

Figure 3:
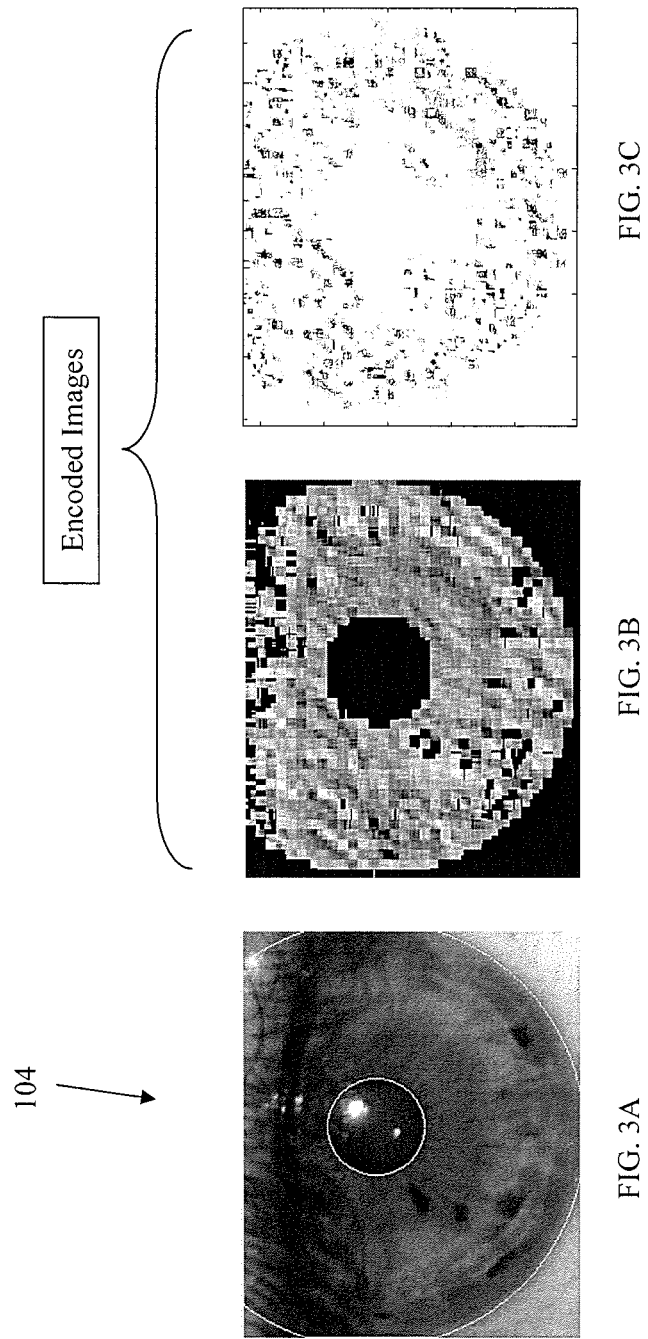
FIG. 3A depicts an edge detection algorithm identifying boundaries of the iris.
FIGS. 3B and 3C depict embodiments of digital representations of an iris.

Initially, pre-process geometrical extraction may acquire the iris image 102 and calculate the pupil size 104. The image may be converted into gray scale. An edge detection algorithm (e.g., Hough transform) may identify the boundaries of the iris (shown in FIG. 3A). Ultimately, this may yield an encoded image (shown in FIGS. 3B and 3C) comprising a digital representation of the radiometric levels of the iris information (e.g., pupil, eyelashes, etc., removed). One skilled in the art would appreciate the many ways pre-process extraction may be performed and the present teachings are not limited to any particular embodiment disclosed herein. If performed on another biometric (e.g., ear, etc.) it may not be necessary to perform this pre-processing, or different pre-processing may be performed that is appropriate for that biometric. What is desirable is to isolate information so that further mathematical processing may be performed, discussed further below.

Next, iris spatially localized features (ISLF) may be calculated. This includes applying pattern encoding 108 (discussed further below in relation to FIG. 5B). In one embodiment, each line of the iris image (e.g., $225^{th}$ line 128 of iris image shown in FIG. 5A) may be decomposed using a wavelet transform process multiple times to form a wavelet family. A wavelet transform procedure may identify the intensity and duration of local radiometric change. Unique local relations may be detected between the transformation's coefficients. These relations are less susceptible to acquisition conditions (such as illumination, ambient light and more).

Figure 4:
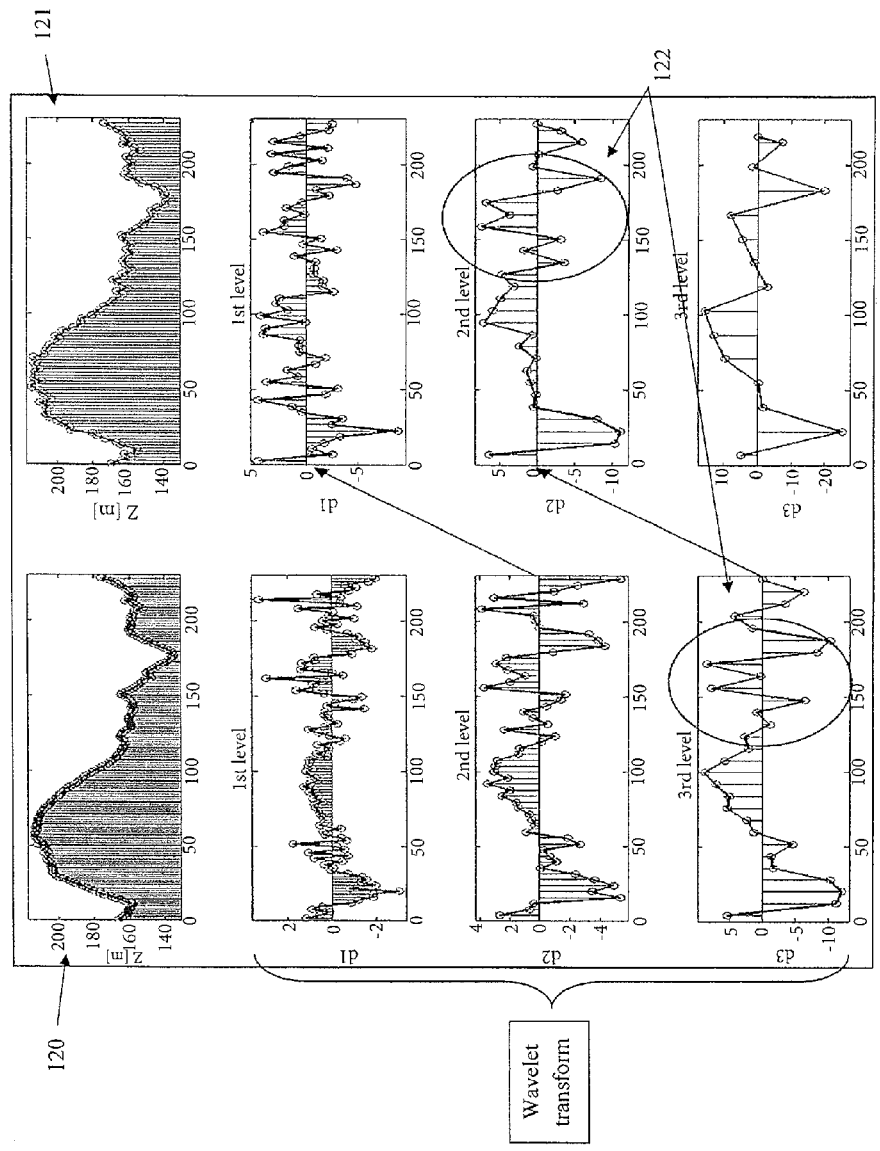
FIG. 4 depicts an example of the radiometric profiles of the same line from two images of the same iris.

Referring now to FIG. 4, shown is an example of the radiometric profiles 120, 121 of the same line from two images of the same iris. This shows 2-D signal analysis, where two profiles differ from each other by a scaling factor. This demonstrates the similarity of phenomena spread spatial proportionally.

The line profiles 120, 121 may be decomposed into three levels (resolutions/frequencies) through a wavelet transform procedure. Strong local relations at different levels of decomposition may indicate local phenomena (trends in the radiometric profile).

Because of the variance of noise (e.g., ambient conditions affecting image capture) between the resolutions of the two images, a match 122 between the two line profiles 120, 121 may be identified on different levels of the waveform transform procedure. Variance may also be introduced by differences in camera lenses, distances, angles, ambient light, etc.

Figure 5A:
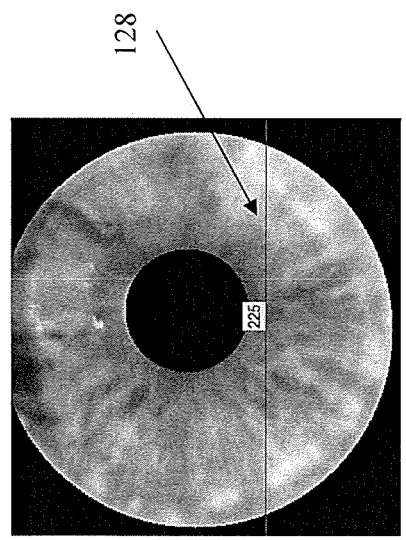
FIG. 5A depicts the 225th line of an iris image.
Figure 5B:
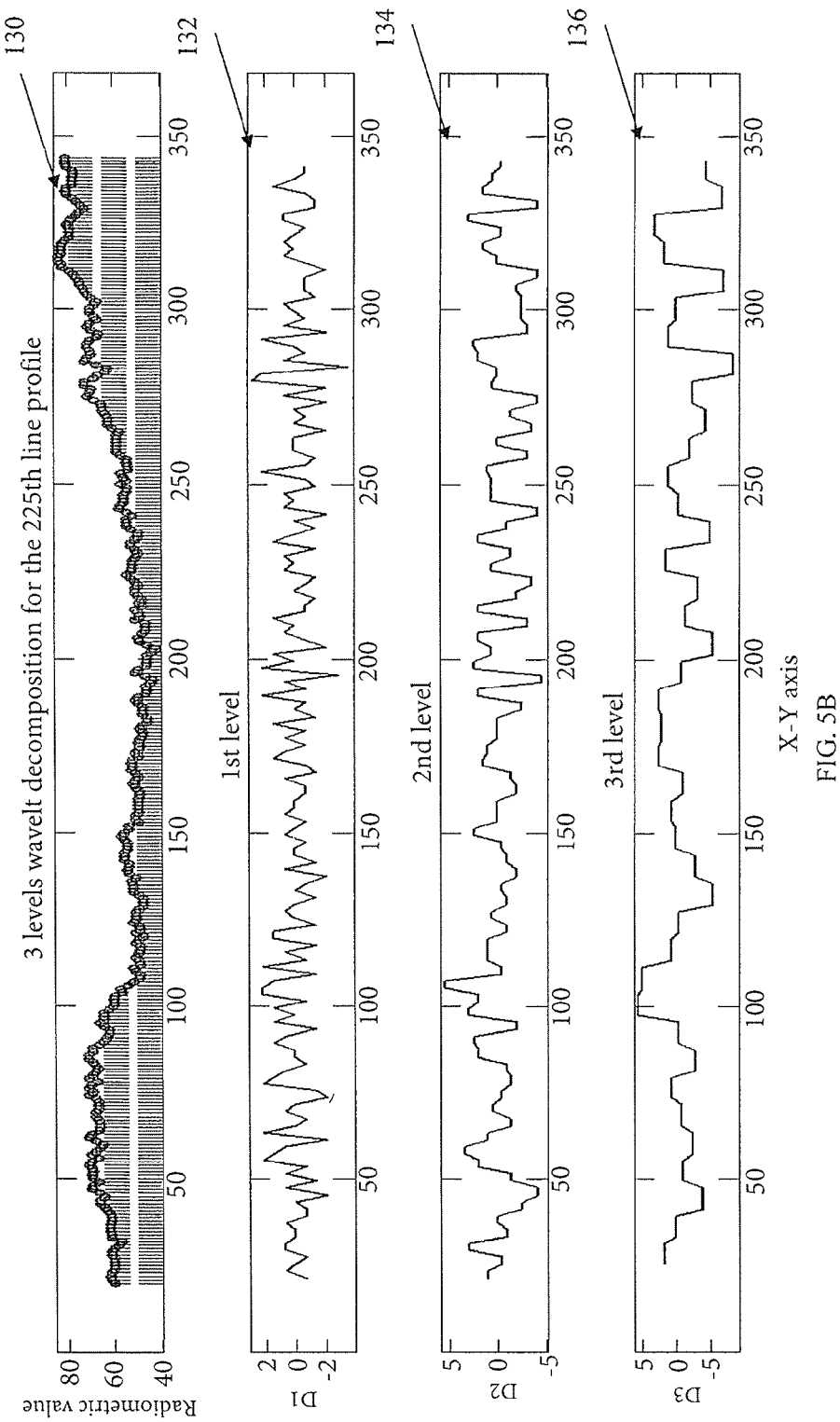
FIG. 5B depicts a radiometric profile of the 225th line of FIG. 5A.

Referring again to pattern encoding (step 108 in FIG. 2), shown in FIG. 5B is the radiometric profile 130 of the 225th line 128 (shown in FIG. 5A) of an iris image. The image may first be encoded into a digital representation of the radiometric levels of the iris in grey scale. The radiometric profile 130 may be decomposed into first level 132, second level 134 and third level 136 wavelet transforms. The X-axes represent the column indexes of the line 128 whereas the Y-axes represent the wavelet coefficients value achieved by the transformation process.

In one embodiment, the HAAR wavelet procedure may be used for wavelet transformation. The two filters may be used in the transformation: (1) High pass filter (the wavelet function) having a vector with two values in the form [−1 +1]; (2) Low pass filter (scaled function) having a vector with two values in the form [+1 +1]. These filters may be moved along the image (e.g., both directions x-y). The wavelet function may search for intensity changes (e.g., trends) and the scaling function may stretch the original signal into lower resolution(s). This may provide for multi-resolution analysis.

In one embodiment, the following mathematical algorithms may be used for the wavelet transformation. For a wavelet mother function (HAAR family):

$$\Psi[i, s] = \begin{cases} 1 \cdot k_s, & \text{for } f_{[2i-1,s]} \\ -1 \cdot k_s, & \text{for } f_{[2i,s]} \end{cases}$$

For a wavelet expansion function (HAAR family):

$$\phi[i, s] = \begin{cases} 1 \cdot k_s, & \text{for } f_{[2i-1,s]} \\ 1 \cdot k_s, & \text{for } f_{[2i,s]} \end{cases}$$

Where $f_{[2i,s]}$ is the location along the signal where the transformation is applied at the specific resolution level (s) and $k_s = 2^{-s/2}$.

Such a process helps to reduce "noise" in the image profile, although not limited thereto. Spatially localized descriptors may indicate the intensity of local radiometric change as well as the duration of this change. This way, it is possible to emphasize strong trends among the radiometric levels of the line profile. The process may be performed by running over the x-axis (column of the profile) and calculating linear relations ($\alpha$) between the wavelet coefficients in each decomposition level and the level of decomposing. Areas where there is a strong relation represent phenomena that occur along a wide area, and are strong features.

Next, interest points may be encoded and localized (step 110 in FIG. 2). Shown in FIG. 5C, the radiometric profile 130 (from FIG. 5B) may be divided by the three wavelet transform levels 132, 134, 136 in order to obtain a strong, unique signal 138 with little noise. This may be done by calculating the ratio between the radiometric value of each column and the $\alpha$ value (e.g., described above). This local transform of the signal represents the signal where spatially localized featured are emphasized. The new signal 138 is less sensitive to illumination conditions and to pupil dilations.

The signal may be calculated using the following algorithm:

$$a_i = \frac{D^3 i - D^1 i}{S^3 - S^1}$$

Where $D^j i$ is the detailed coefficients at the $i^{th}$ pixel location in the j decomposition level. $S^j$ is the scaling value for the j decomposition level. More simplified, one might use $S^1 = 1$ and $S^3 = 4$.

Approximation coefficients:

$$A_i^s = s^{-1/2} \sum_{k=1}^{2} \phi_{s,k} \cdot f_{(2i-k-1)} = \frac{1}{\sqrt{s}} \begin{bmatrix} 1 \cdot k_s \\ 1 \cdot k_s \end{bmatrix} \cdot [\, f_{2i-1} \quad f_{2i} \,]$$

Detailed coefficients:

$$D_i^s = s^{-1/2} \sum_{k=1}^{2} \Psi_{s,k} \cdot f_{(2i-k-1)} = \frac{1}{\sqrt{s}} \begin{bmatrix} 1 \cdot k_s \\ -1 \cdot k_s \end{bmatrix} \cdot [f_{2i-1} \quad f_{2i}]$$

For each set of 2 pixels one can calculate the approximation and detailed coefficients (A & D) and the corresponding α. The final value (R) for the $i^{th}$ pixel location in the template image may be:

$$R_i = \frac{A^3 i}{\alpha_i}$$

The process of generating such a signal 138 may be repeated for each line in the iris image (e.g., line 225 128 shown in FIG. 5A). These signals are used to assemble the iris template, discussed further below.

Figure 6:
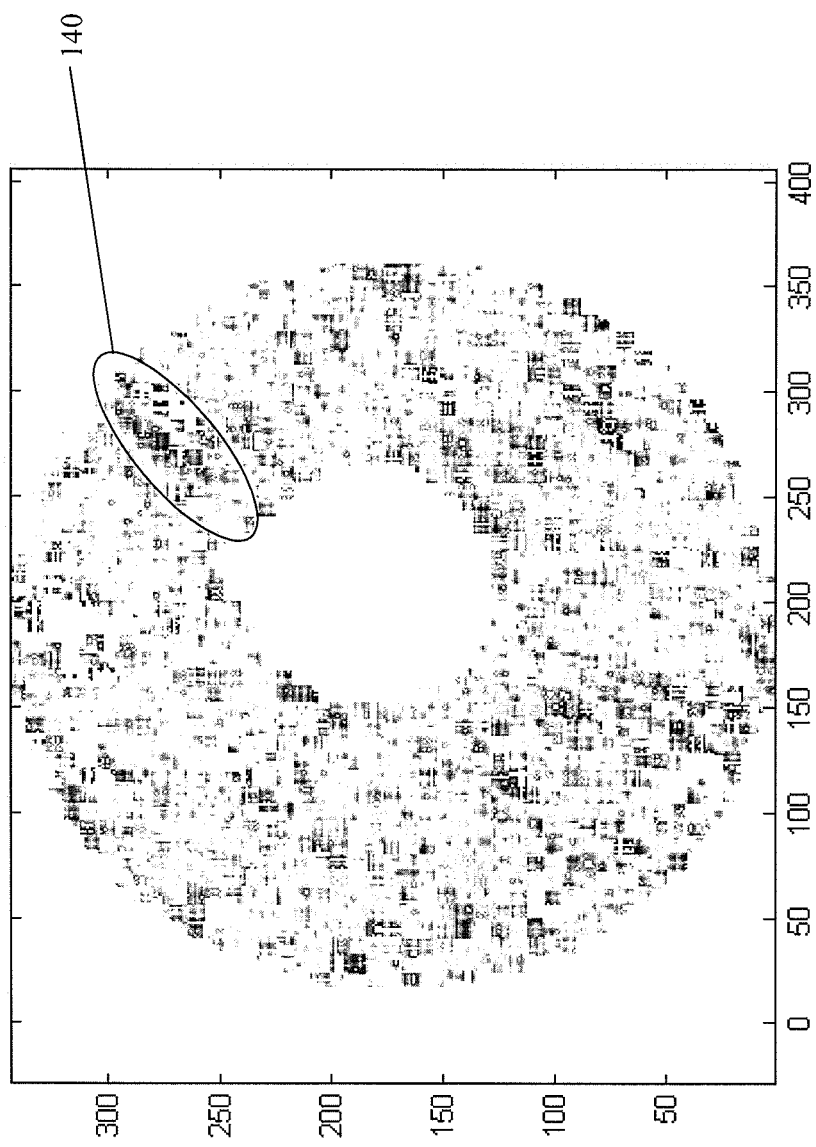
FIG. 6 depicts an iris template.

Next, image coding may be performed (step 112 in FIG. 2). As shown in FIG. 6, a complete iris template may be created by assembling the separate lines. Once the complete iris template is assembled, a 3-dimensional uniqueness model may be calculated for the iris. As shown in FIG. 6, shading (or colors, etc.) may be employed to help identify the contours of the image. For example, red pixels may indicate high intensity contours 140 of the signal (for each line) whereas blue pixels may indicate low intensity, although not limited thereto. In another embodiment, varying intensities of grey-scale colors may be used. Extreme intensities may indicate interest points of localized phenomena 140. One skilled in the art would appreciate that there are many ways to depict the spatially localized features emphasized by the line-by-line signal generation of FIGS. 5B-C and the present teachings are not limited to any particular embodiment disclosed herein.

The areas of high contour value in the assembled iris template may then be identified and ranked. For example, the 10 areas with the highest intensities may be identified, although not limited thereto. It is to be appreciated that any number of intensities may be identified (e.g., 1, 5, 15+, etc.) and the present teachings are not limited to any particular embodiment disclosed herein. One skilled in the art would appreciate that the number of intensities identified on an iris profile may affect reliability of matching as well as computational overhead. The relation (e.g., distance, orientation, etc.) between identified areas of interest may also provide a unique iris signature.

Next, the iris template may be compared to another template to identify an iris (step 114 in FIG. 2). This may include first normalizing the two templates. For example, the two templates may be resized so that they are the same size, or may be rotated so that interest points align, although not limited thereto. In one embodiment, the interest points with the highest intensities in each of the templates may be aligned for comparison. In addition, the intensities of the templates may be adjusted so that their maximum and/or minimum values are the same. What is desired is that normalization help to assure that similar images are being compared. One skilled in the art would appreciate the many techniques for doing so and the present teachings are not limited to any particular embodiment disclosed herein.

Once the templates are normalized, they may be compared to one another. In one embodiment, the Hausdorff distance may be used to measure the differences between areas of interest in the two templates. By subtracting the values between the two templates, if the summation of all differences is less than a predetermined value, then the irises are the same.

In one embodiment, the iris template may be treated as a topographic digital model (e.g., DEM—Digital Elevation Model). The template may be scaled into a pre-defined scaling factor (used for all templates) and the elevation value of each pixel subtracted consistently. The noise information in the template may be neglected because the result of the template process reveals the cleared (significant) information among the original image. Next, the subtracted values may be accumulated. It can be assumed that this factor (summation of all subtracted value) may be 5 times lower than the factor achieved of the original image, and thus is 5 times lower affected by any noise from the acquisition process (e.g., ambient light, pupil dilation, illumination, resolution etc). Because this process is less affected by environmental noises it is lower than previous methods such as that described in the prior art such as U.S. Pat. No. 5,291,560 to Daugman. The template has a local-based structure, thus it is very easy to detect if there is a partial area were the two templates (the tested one and the stored one) do not match (from any reason such as: dirty contact lens, sty or other eye disease, etc). In that case, the specific local area may be removed and the process continued.

The Hausdorff algorithm may use two sets of interest points extracted from two iris images after being compared in their template form (e.g., where A comprises interest points of the tested iris template; B comprises interest points of a compared iris template). These interest points may be the peak points (e.g., shown in FIG. 3C), where the image is regarded as a topographic elevation model. Due to the characteristic of the template calculation these peaks are well defined. Moreover, due to this well-defined structure of peaks (e.g., interest points) the usage of Hausdorff distance may be invariant to: (1) small displacement or inaccuracies of interest points in both datasets; (2) relative scaling & rotation between the two images; and (3) missing interest points in any of the dataset.

In one embodiment, the Hausdorff distance may be computed as follows:
1. Find farthest distant point in A (a) from any point in B.
2. For that point (a) find the closest point in B. H(A,B)
3. Find farthest distant point in B (b) from any point in A.
4. For that point (b) find the closest point in a. H(B,A)
5. The Hausdorff distance is the maximum value between H(A,B) and H(B,A)

The computation time may be of the order of O(nm) point sets of size n and m correspondingly. If in each image 10-20 distinctive interest points are used, the computation time is efficient.

In one embodiment, the following mathematical algorithm for calculating the Hausdorff distance may be used:

$$H(A, B) = \max(h(A, B), h(B, A))$$

where $$h(A, B) = \max_{a \in A} \min_{b \in B} \|a - b\|$$

and $$\|a - b\| = \sqrt{(x_2 - x_1)^2 + (y_2 - y_1)^2}$$

In one embodiment, the identification criteria (preferred value) may be 5% of the pixel size of the image (e.g., for a 300×300 pixel image the identification criteria should be a Hausdorff distance of lower than 15 pixels). In contrast, the prior methods (e.g., U.S. Pat. No. 5,291,560 to Daugman) may provide 30% or more of uncertainty due to noise in the comparison parameter. In cases where the Hausdorff distance is greater than 5%, the algorithm may apply the procedure above for fine-tuning. The present teachings provide a better system for matching because it looks for similarities, whereas prior methods relied upon differences (e.g., Hamming Distance).

The system and method according to the present teachings can utilize varying types of cameras. As a result, it may provide a universal system for iris recognition. This is because it is tolerant of varying acquisition conditions.

The methods according to the present teachings may be employed in software executing on computer readable media. In one embodiment, such software may execute on a mobile device. This may allow the ability to identify individuals in the field, whether by comparing an image taken to one stored locally or to one stored in a database accessible over a network. The processing and comparison functionality may be employed on the mobile device or on a centralized computer (e.g., server). In this way, it is possible to have a smart phone (e.g., iPhone, etc.) running an application for iris recognition, although not limited thereto.

Systems and methods may also be employed as countermeasures to imposters and/or impersonators, although not limited thereto. One way is to shine a light at the iris in order to constrict the iris/pupil and help assure it is a living iris and not just a picture. In one embodiment, a light may be shined in one eye to affect the iris/pupil in the other eye. Not only can the pupillary reflex be verified, but the iris may be recorded at several different pupil diameters. Another way is to observe the natural movement of an eyeball (e.g., measuring nystagmus, tracking eye while text is read, etc.). Yet another way is to invoke a blink reflex, such as with a puff of air.

Various types of light may be used. For example, infra-red (IR) light may be used, which is less affected by noise caused by ambient conditions. However, IR may yield less detailed information and may deter some individuals. The present teachings do not require IR, but it may be used.

Figure 7:
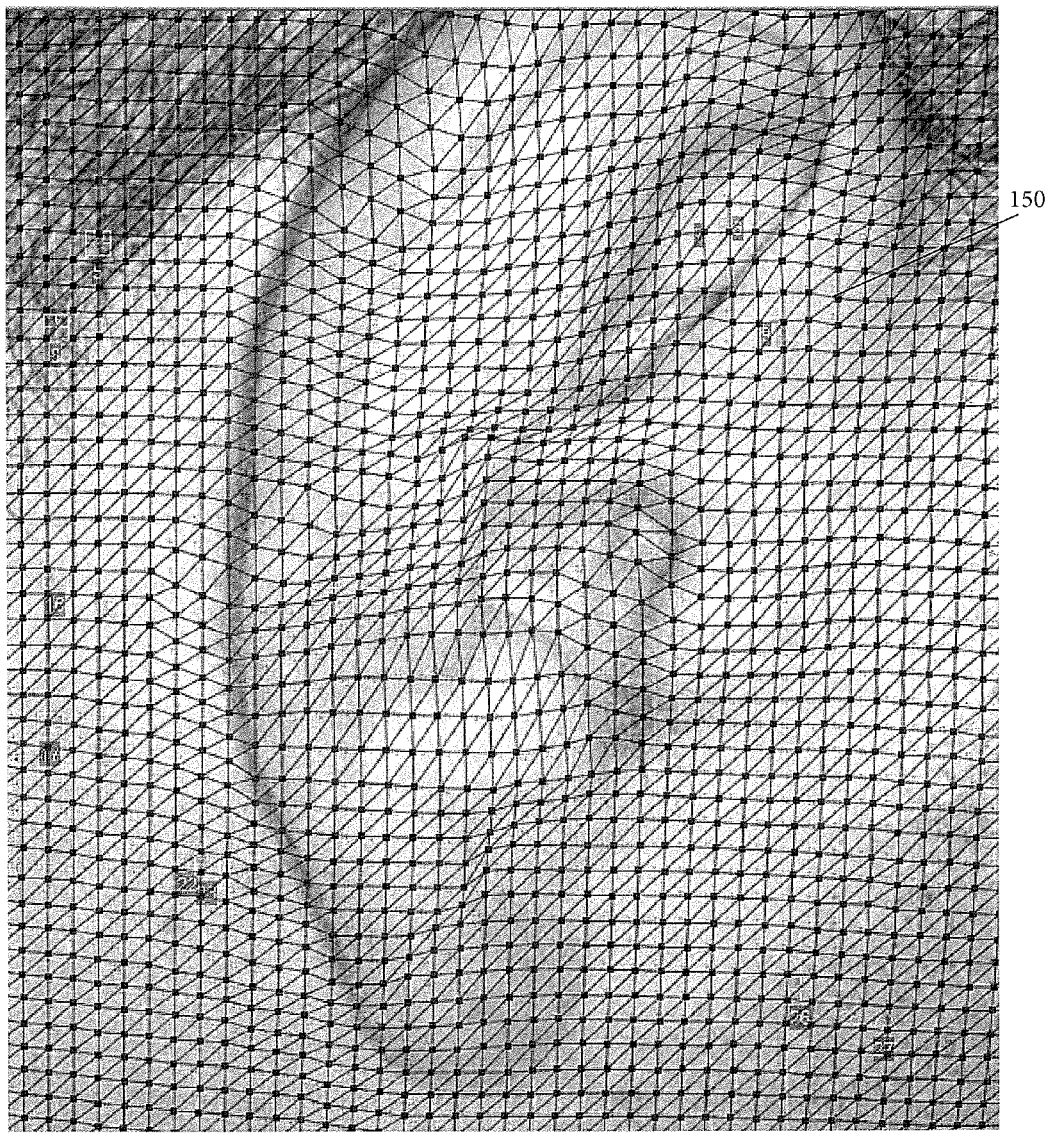
FIG. 7 depicts contour lines of an ear.

Referring now to FIG. 7, it should be noted that the system and method of the present teachings is applicable to other forms of biometrics. This is a unique advantage over previous methods in that multiple biometrics can be enrolled into a database including, for example, ears and fingerprints. In case of failure (e.g., false recognition), it may be preferable to have a back-up system. In addition, some people may not have irises or their irises may be blocked (e.g., corneal blindness). Enrolling another biometric may be preferable in certain applications. For example, baby's ears are unique at birth and such a system may be helpful to identify newborn babies before their irises develop. A combination of the mother's eye and baby's ear may confirm identity at the time of discharge and help prevent baby abductions, although not limited thereto.

Biometric identification according to the present teachings may permit enrollment/recognition by digital image capture devices having varying resolution capabilities (e.g., high resolution camera may be preferred). The capture device may be either stand alone or provided with existing devices such as smart phones, iPhones, tablet computers, iPads, or similar devices, although not limited thereto. This may eliminate the need to purchase high cost devices and allow for widespread use since any number of types of imaging devices may be used.

Using the process described above with reference to the iris, an image of an ear may be taken and encoded into an ear template. However, instead of the radiometric profile of each line, the relative elevation (e.g., contour of 3-D ear image) may be used to identify local phenomena (trends).

As shown in FIG. 7, similar to a topographical map, contour lines 150 represent relative elevations in the ear and can be used to identify interest points (e.g., extreme intensities) with elevation changes. As many lines of information as are available may be used since the present teachings may be tolerant to scaling.

The comparison of two ears may be similar to the comparison of two irises. The images may be compared using identified interest points in each template, as discussed above with reference to the iris. It may be preferable to first normalize the ear templates, for example, to make them the same size.

Figure 8:
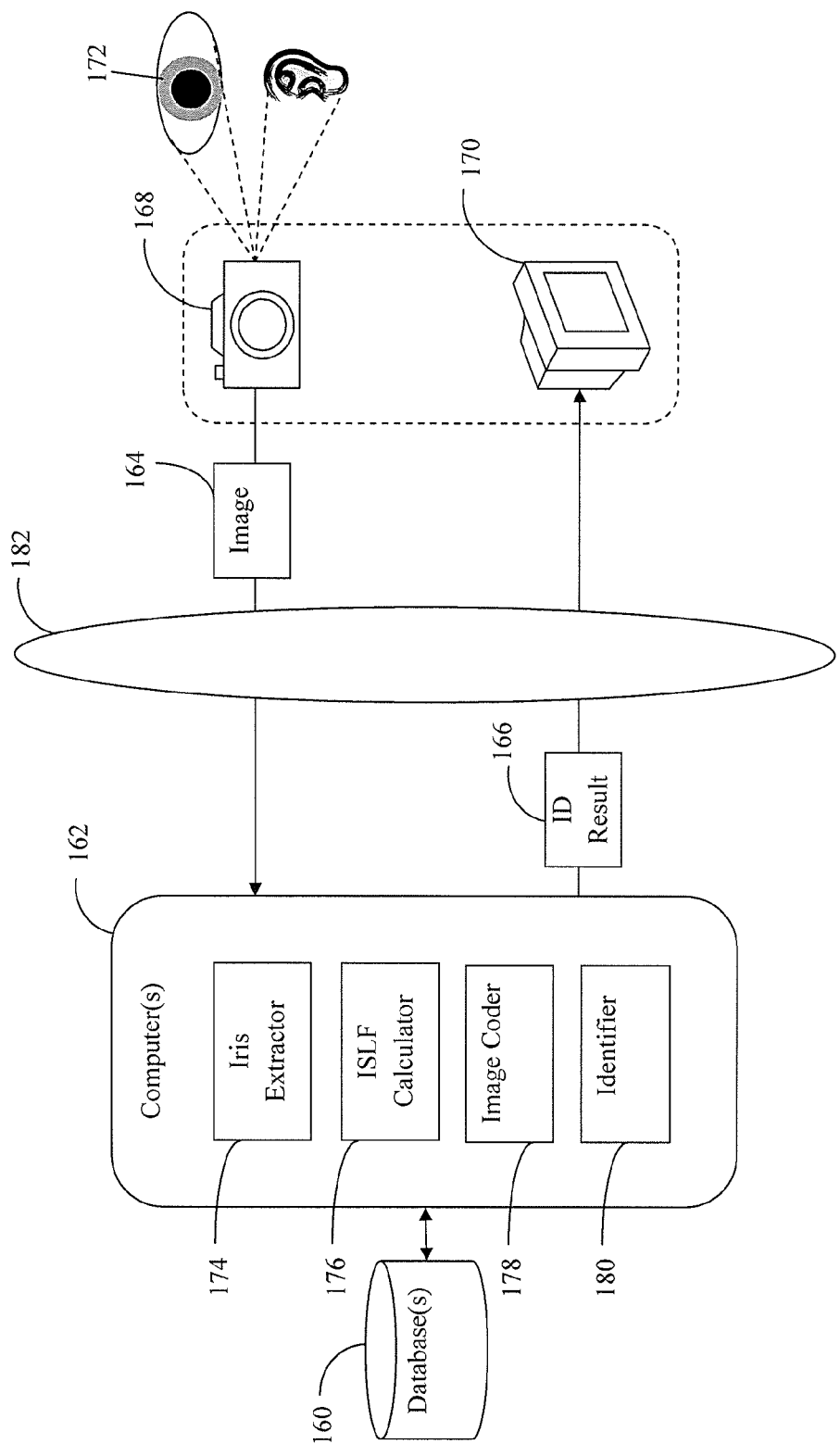
FIG. 8 depicts one embodiment of the system of biometric identification according to the present teachings.

Referring now to FIG. 8, shown is one embodiment of the system of biometric identification according to the present teachings, and it is to be appreciated that the system may be employed with different biometrics (e.g., irises, ears, etc.). As shown, a camera 168 (generically an "image capture device") may obtain an image of an iris 172. It is to be appreciated that any form of camera may be used, avoiding the need for specialized hardware. For example, it could be a general purpose digital camera, a smart phone camera, an iris scanner, or even a surveillance video camera, although not limited thereto. What is desirable is camera technology capable to obtaining an image of the biometric being analyzed. Below, the present teachings will be discussed specifically with regard to irises, although not limited thereto.

One way in which the present teachings are unique to previous methods is that the same algorithm can be used on multiple biometrics. For example, ears, irises, finger prints, etc. may be analyzed using this algorithm. On one embodiment, when analyzing finger prints the radiometric profile may be transformed into a binary profile, and the identification of interest points performed the same way as irises. Moreover, while previous biometric matching was performed on the basis of counting mismatched information, the present teachings are also unique in that they count the match of information (e.g., spatially localized).

An image 164 of the iris (or other biometric) is sent to one or more computers 162 for processing. In one embodiment, communication occurs over a network 182 such as the Internet, although not limited thereto. In this way, centralized server computer(s) 162 may perform processing. In another embodiment, the camera 168 and computer 162 may comprise the same device, such as a mobile device or an iris scanning machine, although not limited thereto.

The computer(s) 162 perform the process for iris recognition described above. An iris extractor 174 may extract iris information from the iris image 164. It may calculate the pupil size, convert the image into gray scale, and perform an edge detection algorithm (e.g., Hough transform) to identify the boundaries of the iris. Such "pre-processing" (steps 102, 104 in FIG. 2) may yield a digital image (e.g., encoded) comprising the iris information (e.g., pupil, eyelashes, etc. all removed).

An ISFL calculator 176 may decompose the encoded image to reduce "noise" in the image profile. Spatially localized descriptors may indicate both the intensity of local radiometric change as well as the duration of change. This way, it is possible to emphasize strong trends in the radiometric levels of the profile. In one embodiment, each line of the encoded image may be decomposed using a wavelet transform process multiple times to form a wavelet family. The radiometric profile may be divided by the wavelet transform levels in order to obtain a strong, unique signal with little noise (see steps 108, 110 in FIG. 2).

An image coder 178 may assemble an iris template and identify interest points (step 112 in FIG. 2). In one embodiment, the iris template may represent a 3-dimensional uniqueness model using shading (or colors, etc.) to help identify the contours of the ISLF signal. High intensities may indicate interest points of localized phenomena. The areas of high contour value in the assembled iris template may then be identified and ranked.

An identifier 180 may normalize the iris template and compare it with stored templates (step 114 in FIG. 2). Stored templates may be stored in one or more databases 160, which may be locally accessible or accessible over a network such as the Internet. Templates for comparison may be resized so that they are the same size, or may be rotated so that interest points align, although not limited thereto. In addition, the intensities of the templates may be adjusted so that their maximum and/or minimum values are the same. The templates, whether normalized or not, may be compared to one another. In one embodiment, the Hausdorff distance is used to measure the differences between areas of interest in the two images.

The speed of matching templates according to the present teachings may be considered in two parts, although not limited thereto:

1. When an acquired image is compared to a stored image for the same person (e.g., verify claim of identity), this analysis can be performed very fast (e.g., less than a second, etc.).
2. When an acquired image is compared to a large number of stored images, this analysis may take longer. However, since the information is spatially located there are known methods of indexing the information to reduce searching time.

Since interest points are spatially localized they can be indexed in a database. In one embodiment, an image area may be split into a matrix of n*n cells. Interest points may be located in one or more of the spatial cells. Each cell may then have a list (index) of all the templates where an interest point is located. When an acquired image is to be compared against images in a database, the database may be searched for images that have interest points in the same cells as the acquired image.

For example, suppose interest points are indexed into a 6*6 matrix and there are 360*360 pixels (meaning each cell covers 60*60 pixels):

| 1 | 7  | 13 | 19 | 25 | 31 |
|---|----|----|----|----|----|
| 2 | 8  | 14 | 20 | 26 | 32 |
| 3 | 9  | 15 | 21 | 27 | 33 |
| 4 | 10 | 16 | 22 | 28 | 34 |
| 5 | 11 | 17 | 23 | 29 | 35 |
| 6 | 12 | 18 | 24 | 30 | 36 |

Next, suppose an acquired image has interest points in cells 8, 22, 29 and 35. This image may be indexed to these cells in the database. The acquired image may only have to be compared to images in the database that have an interest point in at least one (or multiple, or all, etc.) of cells 8, 22, 29 and 35. This may significantly reduce search time. In one embodiment, a 20*20 pixel cell may be sufficient enough for identification (e.g., for 400*400 pixels image there will be a matrix of 20*20 cells).

The identifier 180 may return an ID result 166. In one embodiment, the ID result 166 comprises whether a match was found, and if so, information on the match (e.g., biographical information about the subject associated with the matched template, etc.). The ID result 166 may be displayed on a display 170, although not limited thereto. In one embodiment, the display 170 and the camera 168 comprise the same physical device (e.g., iris scanning machine, mobile device, etc.), although not limited thereto.

In one embodiment, communication between the camera 168, processing computer(s) 162, and display 170 may be over a secure network. This may include a private network or encryption/decryption techniques may be employed, although not limited thereto. This may help to authenticate the sender of data to help ensure that only authorized devices are communicating with the system.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A method for biometric recognition, comprising the steps of:
   decomposing, using a wavelet transform process, a profile of an image of the biometric into a plurality of wavelets at varying decomposition levels;
   determining a relative value for a plurality of pixel locations on the biometric profile;
   determining, from the plurality of wavelets, wavelet coefficient values for each pixel location;
   calculating a signal comprising at least one spatial descriptor by:
   (1) calculating, from the plurality of wavelets, linear relations between the wavelet coefficient values in each decomposition level and a scaling value for each decomposition level, and
   (2) calculating ratios between relative values for the plurality of pixel locations and said linear relations;
   assembling a biometric template using the signal, the biometric template reflecting the at least one spatial descriptor;
   identifying the spatial descriptors in the biometric template; and
   comparing the spatial descriptors in the biometric template to spatial descriptors in a second biometric template.

2. The method of claim 1 wherein:
   the image of the biometric comprises an image of an iris; and
   the steps of decomposing, determining relative values, determining wavelet coefficients, calculating, assembling, identifying, and comparing are repeated on a second image of a second biometric, comprising an image of an ear.

3. The method of claim 2 wherein the iris belongs to a mother and the ear belongs to a child, the method confirming a relationship between the mother and the child.

4. The method of claim 1 wherein the wavelet transform process comprises a Haar wavelet transform process.

5. The method of claim 1 wherein the biometric templates are compared by calculating the Hausdorff distance between the spatial descriptors of each.

6. The method of claim 1 wherein the spatial descriptors are identified by the intensity of an associated signal.

7. The method of claim 1 wherein:
a plurality of lines of the biometric image are decomposed using the wavelet transform process;
signals are calculated using the plurality of wavelets for each of the plurality of lines; and
the biometric template is assembled using signals calculated for each of the plurality of lines.

8. The method of claim 1 wherein the signal is calculated using the following algorithm:

$$\alpha_i = \frac{D^3 i - D^1 i}{S^3 - S^1}$$

Where $D^j i$ is the detailed coefficients at the $i^{th}$ pixel location in the j decomposition level and $S^j$ is the scaling value for the j decomposition level.

9. The method of claim 1 further comprising the step of normalizing the biometric template before the step of comparing.

10. The method of claim 9 wherein the step of normalizing comprises adjusting an extreme intensity spatial descriptor of the biometric template to correspond with an extreme intensity spatial descriptor of the second biometric template.

11. The method of claim 1 further comprising the step of ranking the spatial descriptors.

12. The method of claim 1 wherein the at least one spatial descriptor comprises five or more spatial descriptors.

13. The method of claim 1 wherein the biometric template comprises a three-dimensional model showing intensity contours.

14. The method of claim 13 wherein intensity contours are represented using colors.

15. The method of claim 1 further comprising the step of extracting information from the image before the step of decomposing.

16. The method of claim 15 wherein the step of extracting comprises calculating a pupil size and performing edge detection to identify boundaries of an iris.

17. The method of claim 1 wherein the image comprises an image of an iris.

18. The method of claim 1 wherein the profile comprises a radiometric profile.

19. The method of claim 1 wherein the image comprises an image of an ear.

20. The method of claim 1 wherein the profile comprises a topographic profile.

21. A system for biometric recognition, comprising:
a computer;
a database in electronic communication with the computer;
calculator software executing on the computer, the calculator software:
decomposing, using a wavelet transform process, at least one profile of at least one image of the biometric into a plurality of wavelets at varying decomposition levels;
determining a relative value for a plurality of pixel locations on the at least one biometric profile;
determining, from the plurality of wavelets, wavelet coefficient values for each pixel location; and
calculating at least one signal comprising at least one spatial descriptor by:
(1) calculating, from the plurality of wavelets, linear relations between the wavelet coefficient values in each decomposition level and a scaling value for each decomposition level, and
(2) calculating ratios between relative values for the plurality of pixel locations and said linear relations;
coder software executing on the computer, the coder software:
assembling at least one biometric template using the at least one signal, the at least one biometric template reflecting the at least one spatial descriptor, and
identifying the spatial descriptors in the at least one biometric template; and
identification software executing on the computer, the identification software comparing the spatial descriptors in the at least one biometric template to spatial descriptors in at least one second biometric template, the at least one second biometric template stored in the database.

22. The system of claim 21 wherein:
the at least one image of the biometric comprises an image of an iris and an image of an ear; and
the at least one biometric template comprises biometric templates associated with each of the image of an iris and the image of an ear.

23. The system of claim 22 wherein the iris belongs to a mother and the ear belongs to a child; and the system confirms a relationship between the mother and child.

24. The system of claim 21 wherein the wavelet transform process comprises a Haar wavelet transform process.

25. The system of claim 21 wherein the identification software compares the at least one biometric template to the at least one second biometric template using a Hausdorff distance between the spatial descriptors of each.

26. The system of claim 21 wherein the coder software identifies the spatial descriptors by the intensity of an associated signal.

27. The system of claim 21 wherein:
the calculator software operates on a plurality of lines of the at least one image of the biometric; and
the coder software assembles the at least one biometric template using signals for each of the plurality of lines.

28. The system of claim 21 wherein the at least one biometric template comprises a three-dimensional model showing intensity contours.

29. The system of claim 28 wherein intensity contours are represented using colors.

30. The system of claim 21 wherein the at least one image comprises an image of an iris.

31. The system of claim 21 wherein the at least one profile comprises a radiometric profile.

32. The system of claim 21 wherein the at least one image comprises an image of an ear.

33. The system of claim 21 wherein the at least one profile comprises a topographic profile.

34. The system of claim 21 wherein the computer comprises a plurality of computers.

35. The system of claim 21 further comprising an image capture device, the image capture device providing the at least one image to the computer.

36. The system of claim 35 wherein the image capture device comprises a general purpose digital camera or smart phone.

37. The system of claim 21 further comprising a display device, the display device displaying a result provided by the identification software.

38. The system of claim 21 wherein the at least one image comprises an image of a fingertip.

39. The method of claim 1 wherein the image comprises an image of a fingertip.

40. The method of claim 1 further comprising the steps of:
capturing an image of the biometric; and
authenticating the image by ensuring the biometric depicted is reactive to at least one environmental stimulus.

41. The system of claim 35 further comprising recording software executing on the computer, the recording software recording the biometric's reaction to environmental stimuli to authenticate the biometric;
wherein the image capture device comprises a means for subjecting the biometric to at least one environmental stimulus.

42. The system of claim 35 wherein the image capture device does not require contact with the target biometric.

43. The method of claim 1 wherein:
the image of the biometric comprises an image of an iris; and
the steps of decomposing, determining relative values, determining wavelet coefficients, calculating, assembling, identifying, and comparing are repeated on a second image of a second biometric, comprising an image of a fingertip.

44. The method of claim 43 wherein the iris belongs to a mother and the fingertip belongs to a child, the method confirming a relationship between the mother and the child.

45. The system of claim 21 wherein:
the at least one image of the biometric comprises an image of an iris and an image of a fingertip; and
the at least one biometric template comprises biometric templates associated with each of the image of an iris and the image of a fingertip.

46. The system of claim 45 wherein the iris belongs to a mother and the fingertip belongs to a child; and the system confirms a relationship between the mother and child.

47. They system of claim 41 wherein the biometric comprises an eye and the at least one environmental stimulus comprises a change in illumination, the change in illumination causing a reaction in pupil dilation, thereby confirming the biometric is a live eye.

48. A method for biometric recognition, comprising the steps of:
decomposing a profile of an image into a plurality of wavelets using a wavelet transform process;
calculating a signal using the plurality of wavelets;
assembling a template using the signal, the signal being calculated using the following algorithm:

$$\alpha_i = \frac{D^3 i - D^1 i}{S^3 - S^1}$$

wherein $D^j i$ is the detailed coefficients at the $i^{th}$ pixel location in the j decomposition level and $S^j$ is the scaling value for the j decomposition level;
identifying a plurality of areas of interest in the template; and
comparing the template to a second template using the plurality of areas of interest.

* * * * *